US007629116B2

(12) United States Patent
Ott

(10) Patent No.: US 7,629,116 B2
(45) Date of Patent: Dec. 8, 2009

(54) TYPE I INTERFERON-INDUCIBLE PROTEINS TO DETECT VIRAL INFECTION

(75) Inventor: Troy L. Ott, Moscow, ID (US)

(73) Assignee: Idaho Research Foundation, Moscow, ID (US)

(*) Notice: Subject to any disclaimer, the term of this patent is extended or adjusted under 35 U.S.C. 154(b) by 892 days.

(21) Appl. No.: 10/441,418

(22) Filed: May 19, 2003

(65) Prior Publication Data
US 2004/0009472 A1 Jan. 15, 2004

(51) Int. Cl.
C12Q 1/70 (2006.01)
(52) U.S. Cl. .................................................. 435/5
(58) Field of Classification Search .................. 435/5, 435/6, 330; 436/510, 501, 512, 514, 811; 424/130.1
See application file for complete search history.

(56) References Cited

U.S. PATENT DOCUMENTS

| | | | |
|---|---|---|---|
| 5,175,113 A | 12/1992 | Nissen | |
| 5,194,245 A | 3/1993 | Carter | |
| 5,198,350 A | 3/1993 | Horisberger et al. | |
| 5,466,585 A | 11/1995 | Horisberger et al. | |
| 5,739,290 A | 4/1998 | Horisberger et al. | |
| 5,776,690 A | 7/1998 | Vojdani | |
| 5,863,742 A | 1/1999 | Oh | |
| 5,869,264 A | 2/1999 | Horisberger et al. | |
| 6,030,785 A | 2/2000 | Katze | |
| 6,180,102 B1 | 1/2001 | Hanai et al. | |
| 6,200,559 B1 | 3/2001 | von Wussow | |
| 2002/0192838 A1* | 12/2002 | Ott .......................... | 436/510 |
| 2003/0027176 A1 | 2/2003 | Dailey | |
| 2004/0209800 A1* | 10/2004 | Mushinski et al. ............ | 514/12 |

FOREIGN PATENT DOCUMENTS

| | | |
|---|---|---|
| EP | 0 725 081 B1 | 1/2003 |
| EP | 1 489 416 A1 | 12/2004 |

OTHER PUBLICATIONS

Fields. Fields Virology. Lippincott Williams & Wilkins Publishers; Aug. 2001, p. 340-342.*
Von Wussow et al. The interferon-induced Mx-homologous protein in people with symtomatic HIV-1 infection. AIDS 1990, vol. 4, p. 119-124.*
Rump et al. Common variable immunodeficiency (CVID) and MxA-protein expression in blood leucocytes. Clin. Exp. Immunol. 1995, vol. 101, p. 89-93.*
Roers et al. MxA gene expression after live virus vaccination: a sensitive marker for endogenous type I interferon. The Journal of Infectious Diseases, 1994, vol. 169, p. 807-813.*
Chieux et al. The MxA protein levels in whole blood lysaates of patients with various viral infections. Journal of Virological Methods, 1998, vol. 70, 183-191.*
Charleston, B. and Stewart, H. J. (1993) "An interferon-induced Mx protein: cDNA sequence and high level expression in the endometrium of pregnant sheep" Gene 137:327-331.*
U.S. Appl. No. 60/329,740.*

Chieux et al. The MxA protein levels in whole blood lysates of patients with various viral infections. Journal of Virological Methods, 1998, vol. 70, pp. 183-191.*
Muller-Doblies et al. Innate immune responses of calves during transient infection with a noncytopathic strain of bovine viral diarrhea virus. Clinical and Diagnostic Laboratory Immunology. Mar. 2004, vol. 11, No. 2, 302-312.*
Chieux et al. The MxA protein levels in whole blood lysaates of patients with various viral infections. Journal of Virological Methods, 1998, vol. 70, 183-191.*
Charleston, B. and Stewart, H. J. (1993) "Aan interferon-induced Mx protein: cDNA sequence and high level expression in the endometrium of pregnant sheep" Gene 137:327-331.*
U.S. Appl. No. 60/329,740, (2001).*
Bazzigher, L, et al., "Mx genes show weaker primary response to virus than other interferon-regulated genes", Virology, 186:154-160 (1992).
Chieux , V et al., "The MxA protein levels in whole blood lysates of patients with various viral infections", J. of Virological Methods, 70:183-191 (1998).
Fernandez, M, et al., "In vivo and in vitro induction of MxA protein in peripheral blood mononuclear cells from patients chronically infected with Hepatitis C Virus", J. of Infectious Diseases, 180:262-267 (1999).
Forster, J, et al., "MxA protein in infants and children with respiratory tract infection", Acta Paediatr, 85:163-167 (1996).
Haller, O, et al., "Mx proteins: mediators of innate resistance to RNA viruses", Rev. Sci. Tech. Off. Int. Epiz. 17(1):220-230 (1998).
Halminen, M, et al, "Expression of MxA protein in blood lymphocytes discriminates between viral and bacterial infections in febrile children", Pediatric Research, 41(5):647-650 (1997).
Muller-Doblies, D, et al, "In vitro and in vivo detection of Mx gene products in bovine cells following stimulation with alpha/beta interferon and viruses", Clinical and Diagnostic Laboratory Immunology, 9(6):1192-1199 (Nov. 2002).
Nieforth, Ka, et al., "Use of an indirect pharmacodynamic stimulation model of MX protein induction to compare in vivo activity of interferon alfa-2a and a polyethylene glycol-modified derivative in healthy subjects", Clin. Pharmacol. Ther., 59:636-646 (1996).
Oh, Sk, et al., "Quantitation of interferon-induced Mx protein in whole blood lysates by an immunochemiluminescent assay: elimination of protease activity of cell lysates in toto", J. of Immunological Methods, 176:79-91 (1994).
Roers, A, et al., "MxA gene expression after live virus vaccination: a sensitive marker for endogenous Type I Interferon", J. of Infectious Diseases, 169:807-813 (1994).
Rump, Ja, et al., "Common variable immunodeficiency (CVID) and MxA-protein expression in blood leucocytes", Clin. Exp. Immunol., 101:89-93 (1995).
Von Wussow, et al., "The interferon-induced Mx-homologous protein in people with symptomatic HIV-1 infection", AIDS, 4:119-124 (1990).
Horisberger and Staritzky, "Expression and Stability of the Mx Protein in Different Tissues of Mice, in Response to Interferon inducers or to influenza virus infection.", J. Interferon Res., 9:583-590 (1989).
Halminen, M, et al, "Expression of MxA Protein in Blood Lymphocytes Discriminates between Viral and Bacterial Infections in Febrile Children.", Pediatric Research, 41(5):647-650 (1997).

\* cited by examiner

Primary Examiner—Emily M. Le
(74) Attorney, Agent, or Firm—Howard Eisenberg, Esq.

(57) ABSTRACT

A method for determining the presence of a viral infection in an animal not known to have been infected with a virus or other disease-causing microbial organism by determining the level of Mx protein or other Type I Interferon-inducible protein in the animal.

15 Claims, No Drawings

US 7,629,116 B2

TYPE I INTERFERON-INDUCIBLE PROTEINS TO DETECT VIRAL INFECTION

Pursuant to 35 U.S.C. §200 to §212, it is hereby acknowledged that the U.S. Government has certain rights in the invention described herein, which was supported in part by contract number P20 RR15587 from the National Institutes of Health and contract numbers USDA-FAH#IDA02-AHD98 and USDA-NRI00-35203-9185 from the United States Department of Agriculture.

FIELD OF THE INVENTION

The invention pertains to the field of diagnostic tests to determine whether an individual is infected with a virus. More specifically, the invention pertains to the field of diagnostic tests to determine whether an asymptomatic individual who is not clinically ill or known to be infected with a virus has been infected with a virus.

BACKGROUND OF THE INVENTION

Throughout the world, animals are routinely being shipped from farm to farm. Animals are also regularly imported or exported across state and national borders. Although these animals may appear clinically healthy with no signs of disease, the possibility exists that many of these animals may harbor potentially serious viral infections. Such animals may later become ill with a disease. More seriously from an economic point of view is that many asymptomatic carriers of viral infections may never show signs of disease but yet will continue to shed virus to other animals of a herd or flock. These asymptomatic carriers of viral infections, upon being introduced into a new herd or flock, present a significant risk of infection to the other animals in their new environment.

At present, there are a small number of tests that are routinely performed on apparently healthy animals to ensure that they will not present a threat in their new surroundings. Most notable of these tests is the Coggins test which is performed on horses prior to shipping to ensure that the horse is not infected with Equine Infectious Anemia, a disease which is transmitted from one horse to another by blood sucking insects. Such tests, however, are specific for particular viral diseases and, even if it were possible, it would be economically and physically impractical to test animals for every known viral disease prior to shipping. Moreover, tests are unavailable for the detection of most viral diseases.

Accordingly, the viral infection status of animals is not known before shipping. Yet, knowledge of the viral-infection status of asymptomatic shipped animals is probably the most critical aspect in preventing disease outbreaks. There is a critical need for a means for determining viral infection status of animals before they are shipped.

Knowledge of viral infection status is also critical in the case of an existing outbreak of disease. In recent years several outbreaks of highly contagious viral diseases have occurred. Most notable among these is the foot-and-mouth disease (FMD) outbreak that began in 2001 in England. This outbreak affected thousands of farms and thousands of animals were found to be infected with the FMD virus.

In outbreaks like these, which are typically due to viruses, animals that are suspected of having been infected with the virus are slaughtered in order to control the disease. The slaughtered animals are then tested to determine if they did, indeed, harbor the virus. Because asymptomatic animals from the farm of the virus-positive animal may have been exposed to the virus, these other animals are likewise destroyed.

This slaughter of asymptomatic, possibly exposed animals is done as a precaution because there presently are insufficient tests to determine whether the animals have been infected. In a great many of the cases, it is possible that most if not all of the slaughtered animals were not infected, and so truly posed no danger of spreading the disease. Unfortunately, because of the lack of definitive testing to determine whether or not the animals are virally infected, the slaughter program is a necessary step towards preventing the further spread of the virus.

In addition to the lamentable and unnecessary loss of animal life, such non-discriminating slaughter programs are extremely disruptive to the farmer who loses all of his livestock and to the agricultural economy of the region or the country. Moreover, the costs of such slaughter programs are high and include compensation of the farms for the destruction of the animals. Such compensation, however, is typically insufficient to truly recompense the farmer as it often takes several years to rebuild a lost herd and to make the farm economically viable once more.

A significant need exists for a method to screen asymptomatic animals suspected of being infected with a virus to determine whether or not the animals are infected.

A similar need exists relating to the movement of people throughout the world. In the world of today, people move from one country to the next with little or no knowledge as to whether or not people are harboring potentially lethal viral infections. Although it may never be practical to routinely test all people for infection before travel, if a test for viral infection existed, people that are traveling from a country that is experiencing an outbreak of a viral disease could be tested. Such testing could be used, for example in the case of ebola virus, to prevent the spread of the terrible disease caused by this virus to countries where the virus does not presently exist. Accordingly, as with animals, a significant need exists for a test that can be used to determine viral-infection status in humans.

Mx proteins are monomeric GTPases, which, depending on the species of animal and type of virus, are potent inhibitors of viral replication (Samuel, Virology 183:1-11 (1991)). The sequences of Mx proteins from various species, including sheep, cattle, pigs, and horses, are publicly available through GenBank and have been assigned GenBank Accession numbers X66093, U88329, M65087, and U55216, respectively. Although the antiviral effects of Mx are generally directed against negative-stranded RNA viruses (e.g. orthormyxovirus), their expression is induced in all cells that possess Type I interferon (IFN) receptors.

It has been reported that the gene for Mx protein does not primarily respond to viral infections, but rather is secondarily induced in response to an elevation in virus-induced IFN. Bazzigher, L., et al., Virology, 186:154-160 (1992). Elevations in Mx protein are present in both acute and chronic viral infections. Fernandez, M., et al., J. Infectious Diseases, 180: 262-267 (1999). Induction of Mx protein has been used with patients suffering from an infection to determine whether the illness was due to a viral or bacterial infection. Halminen, M, et al., Pediatric Research, 41(5):647-650 (1997); Forster, J., et al., Acta Paediatr., 85:163-167 (1996); Chieux V., J. Virological Methods, 70:183-191 (1998), and Haller et al., Rev. Sci. Tech. 17:220-230 (1998), and U.S. Pat. Nos. 5,198,350 (Horisberger) and 6,180,102 (Hanai). Determinations of Mx protein have been utilized as a method for determining levels of interferon in patients known to be suffering from an infectious disease. U.S. Pat. No. 6,200,559 (von Wussow); von Wussow, P., et al., AIDS, 4(2):119-124 (1990), Nieforth, K A, et al., Clinical Pharmacology & Therapeutics, 59(6):636-646 (1996); and Oh, SK, J. Immunological Methods, 176:79-91

(1994). Mx protein has also been used as a marker for interferon production to determine the response to vaccination. Roers, A., et al., J. Infectious Diseases, 169:807-813 (1994). It has also been reported that Mx protein levels are elevated in illnesses due to autoimmunity. Rump, J A, Clin. Exp. Immunol., 101:89-93 (1995).

The prior art thus discloses elevation in levels of Mx protein in patients showing signs of a disease or in subjects that were known to be exposed to a virus or to a vaccine. There is no indication in the prior art that Mx protein determination may be useful as a diagnostic tool in an animal free of signs of a viral disease, which animal has not recently been knowingly exposed to a virus or been recently vaccinated.

SUMMARY OF THE INVENTION

It has been discovered that Mx protein is useful as a screening parameter for detection of viral infection in animals. In one embodiment, the invention is a method for determining the presence of a viral infection in an animal. According to this embodiment, the animal is not known to have been infected with a virus or other disease-causing microbial organism and, preferably the animal is not showing any clinical signs consistent with a viral infection. The level of Mx protein in the animal is determined and compared to that of animals of the same species known to be virus-free. A level of Mx protein in a subject animal above that which is found in animals of the same species that are known to be free of viral infection indicates the presence of a viral infection in that subject animal.

Detection of viral infection by the method of the invention is facilitated by the fact that Mx levels are very low in uninfected, non-pregnant animals or humans and Mx levels are very high for several weeks following infection. Typically, animal producers quarantine new arrivals for a period of time to determine of symptoms of disease will be present. The test according to the method of the invention provides an indication as to whether a newly arrived animal has experienced a viral infection during the period of 3 to 4 weeks prior to arrival as the evidence of infection typically lingers for 3 to 4 weeks post-infection.

In an alternative embodiment, the level of Mx protein in the animal is compared to that of animals of the same species known to be virally infected. A level of Mx protein in the animal being tested lower than that found in virally infected animals of the same species indicates the absence of viral infection in the subject animal.

In another embodiment, the invention is a kit for determining the presence or absence of viral infection in a subject animal. According to this embodiment, the kit contains a receptacle for holding a test sample, one or more reagents which when combined with the test sample enable an operator to visually determine the level of Mx protein in the test sample, and instructions for determining the level of Mx protein in the sample. Preferably, the instructions further indicate how to determine the presence or absence of a viral infection in an animal based upon the level of Mx protein in the test sample.

It has also been unexpectedly discovered that Type I Interferon inducible proteins in addition to Mx protein are useful as a screening parameter for detection of viral infection in animals. In one embodiment, the invention is a method for determining the presence of a viral infection in an animal. According to this embodiment, the animal is not known to have been infected with a virus or other disease-causing microbial organism and, preferably the animal is not showing any clinical signs consistent with a viral infection. The level of a Type I Interferon-inducible protein in the animal is determined and compared to that of animals of the same species known to be virus-free. A level of the protein in a subject animal above that which is found in animals of the same species that are known to be free of viral infection indicates the presence of a viral infection in that subject animal.

In an alternative embodiment, the level of a Type I Interferon-inducible protein in the animal is compared to that of animals of the same species known to be virally infected. A level of the protein in the animal being tested lower than that found in virally infected animals of the same species indicates the absence of viral infection in the subject animal.

In another embodiment, the invention is a kit for determining the presence or absence of viral infection in a subject animal. According to this embodiment, the kit contains a receptacle for holding a test sample, one or more reagents which when combined with the test sample enable an operator to visually determine the level of a Type I Interferon-inducible protein in the test sample, and instructions for determining the level of the protein in the sample. Preferably, the instructions further indicate how to determine the presence or absence of a viral infection in an animal based upon the level of this protein in the test sample.

DETAILED DESCRIPTION OF THE INVENTION

A first embodiment of the invention is a method for determining the viral infection status of an animal. In accordance with this embodiment of the invention, a biologic sample is obtained from a test animal and the level of Mx protein expression in the animal is determined by determining the level of Mx protein or of an indicator of Mx protein expression in the sample. The level of Mx protein expression in the test animal is compared with that of a control animal of the same species, wherein the infection status of the control animal is known. The viral infection status of the test animal is determined by this comparison.

Alternatively, the invention is a method for determining the viral infection-status of an animal by obtaining a biological sample from a test animal and determining the level of expression of a Type I Interferon-inducible protein or of an indicator of expression of the protein in the sample. The level of the protein in the test animal is compared with that of a control animal of the same species, wherein the infection status of the control animal is known. The viral infection status of the test animal is determined by this comparison.

In addition to Mx protein, any Type I Interferon-inducible protein that is elevated in the presence of viral infection is suitable for the present invention. Preferably, the Type I Interferon-inducible protein is one of the following proteins: 2',5' oligoadenylate synthetase, β2-microglobulin, IFN regulatory factor 1, ubiquitin cross-reactive protein (also known as "interferon stimulated gene factor 17" ("ISG-17")). Most preferably, the Type I inducible protein other than Mx protein is ISG-17.

The following description of the invention, including the Examples, is illustrated by Mx protein. However, it is to be understood that this description is applicable to other Type I Interferon-inducible proteins, collectively and individually, including the proteins listed in the preceding paragraph.

Thus, unless specifically indicated otherwise in the description that follows, reference to Mx protein may be interpreted as being "Mx protein or other Type I Interferon-inducible protein". The claims that follow the description, however, are specific. Thus, a reference in the claims to Mx protein means Mx protein only, a reference in the claims to Type I Interferon-inducible proteins includes Mx protein, and a reference in the claims to Type I Interferon-inducible proteins other than Mx protein excludes Mx protein.

The animal that is tested may be of any species that produces an increase in Mx protein, or other Type I Interferon-inducible protein, either directly or indirectly in response to a viral infection. Animals suitable for the method of the invention include vertebrates, such as mammals, reptiles, amphibians, birds, and fish. Examples of mammals that may be tested for viral status according to the method of the invention include members of the orders of primates such as humans, monkeys and apes, perissodactyla such as horses and rhinoceros, artiodactyla such as pigs, cattle, sheep, goats, camels, llamas, and hippopotamus, carnivora such as dogs, cats, bears, and weasels, pinnipedia such as seals and sea lions, lagomorpha such as rabbits and hares, rodentia such as squirrels, rats, and mice, cetacea such as whales, dolphins, and porpoises, and proboscidea such as elephants.

The biologic sample that is obtained may be any bodily fluid or tissue in which the level of Mx protein, or other Type I Interferon-inducible protein, is elevated, either directly or indirectly, in response to a viral infection. Suitable fluids may vary depending on the type of animal to be tested but generally include fluids such as milk, saliva, urine, or nasal, ocular, or vaginal secretions, or whole blood, plasma, or serum. Fluids may also include those that are produced as part of a pathologic process such as exudates or transudates, such as from the skin, the pleural or peritoneal cavity, the oral cavity, or from the digestive, respiratory, or genital system. Examples of tissues that are suitable include blood cells, biopsy samples, skin, and cellular exudates such as from the oral cavity, the genitourinary, respiratory, or digestive systems.

The biologic sample is preferably obtained from the test animal during the time following exposure to a virus which is sufficiently late so that the animal will express increased levels of Mx protein, or other Type I Interferon-inducible protein, but which is not so late that the animal will no longer be expressing increased levels of Mx protein or other Type I Interferon-inducible protein in response to the viral infection. Practically, however, the time of testing is immaterial because, generally, it is not known whether or not the test animal has been exposed to a virus. Consequently, the preferred time for testing will not be capable of determination. In the event that there is a suspected date of exposure to a virus, the date of testing should be sufficiently after the suspected date so that the increased expression of Mx protein or other Type I Interferon-inducible protein will have occurred. This date will vary depending upon the species of animal and upon the virus that is suspected to have infected the test animal.

The level of Mx protein or other Type I Interferon-inducible protein expression in the sample may be determined by any method that permits this determination to be made. Suitable methods include detecting the Mx protein itself, such as by ELISA test, an assay based on Mx protein function, or a Western blot. Suitable methods also include detecting increased levels of Mx or other Type I Interferon inducible protein mRNA, such as by Northern blot, slot blot, or PCR. In a preferred embodiment, the level of Mx, or other Type I Interferon-inducible, protein expression is determined by detecting the level of Mx protein, or other Type I Interferon-inducible protein, present in a sample by a calorimetric assay based, for example, on the binding of an antibody to the Mx protein, similarly to the methods that are used in human home pregnancy diagnostic kits.

The level of Mx protein, or other Type I Interferon-inducible protein, expression in the test animal is compared to the level of Mx protein, or other Type I Interferon-inducible protein, expression in a control animal of the same species of which the viral infection status is known. Preferably, the control animal is one that is not infected with a virus and is not in an early stage of pregnancy and that, therefore, has a baseline low level of Mx protein, or other Type I Interferon-inducible protein, expression. Preferably, the control animal is an historic control.

In the preferred situation where the control animal is a viral negative, that is not infected with a virus, and therefore has a low level of Mx protein, or other Type I Interferon-inducible protein, expression, a negative test result is one in which the level of Mx protein, or other Type I Interferon-inducible protein, expression in the test animal is not significantly elevated above that of the control. The negative test result in this situation indicates lack of viral infection in the test animal. Conversely, a level of Mx protein, or other Type I Interferon-inducible protein, expression that is significantly elevated above that of the control is a positive test result that indicates that the test animal is infected with a virus.

For purposes of this application, a "significant elevation in level of Mx protein expression, or other Type I Interferon-inducible protein expression, above that of a control" is a level of Mx protein that is at least two times that present in a non-infected animal. In many animal species, Mx protein is not expressed in the absence of a viral infection. In these animals, any level of Mx protein that is detected is considered to be a significant elevation. Likewise, in many animal species, one or more Type I Interferon-inducible proteins other than Mx protein are not expressed in the absence of a viral infections. Thus, any level of such protein that is detected is considered to be a significant elevation.

In the less preferred situation where the control animal is a viral positive, that is that it is known to be infected with a virus that stimulates an increase in Mx protein expression, a negative test result is one in which the level of Mx protein expression in the test animal is not significantly lower than that of the control. Similarly, a viral positive control animal may be utilized with a Type I Interferon-inducible protein other than Mx protein. The negative test result in this situation indicates that the test animal is infected with a virus. Conversely, a level of Mx protein, or other Type I Interferon-inducible protein, expression that is significantly lower than that of the control is a positive test result that indicates that the test animal is free of viral infection.

It has been determined that levels of Mx protein, as well as one or more other Type I Interferon-inducible proteins, may be elevated in some species of animals during pregnancy and in the presence of an autoimmune disease. The presence of either of these conditions may lead to a false positive result, that is an elevation in Mx protein, or other Type I Interferon-inducible protein, that would otherwise indicate a viral infection.

The kit of the invention is preferably based on an enzyme linked assay (ELISA), such as what is known as an "immunometric" or "sandwich" assay. Such an assay involves "sandwiching" a ligand (such as an antigen) with two or more receptor molecules (such as antibodies) which complex with the ligand in a non-interfering manner and at different epitopic sites. Examples of such assays are described in David et al., U.S. Pat. No. 4,486,530. In other preferred alternatives, the kit may be based on chemiluminescence assays, enhanced luminescence assays, and radioimmunoassays. In a preferred embodiment, the kit includes a package, which package houses a test surface, such as a slide or multiple test wells, that is bound to an antibody that will bind to an epitope of the protein of interest, such as Mx protein, a container housing a second antibody that will bind to a second epitope of the protein, which second antibody is labeled, a container housing a standard sample having a baseline concentration of the protein, a reagent that when contacted to the labeled second antibody permits the relative amount of the protein present to be visualized, and instructions for use of the kit to determine whether a test sample contains an amount of Mx protein indicative of virally-infected or uninfected status.

The kit of the invention for determining viral infection status by determining the relative level of Mx protein, or other Type I Interferon-inducible protein, in a test sample compared to a control may be formulated in many different ways, which ways will be apparent to those skilled in the art upon reading the description herein. It is intended that these various formulations of the kit of the invention are included in the invention.

All articles and patents cited in this application are incorporated herein by reference.

Further modifications, uses, and applications of the invention described herein will be apparent to those skilled in the art. It is intended that such modifications be encompassed in the following claims.

The invention claimed is:

1. A method for screening an animal for being an asymptomatic carrier of a viral infection associated with increased expression of Mx protein comprising determining the level of expression of Mx protein in a first animal not known to have been infected with a virus or other disease-causing microbial organism and not showing any clinical signs consistent with a viral infection, and comparing the level of expression of said protein in the animal to that of a second animal of the same species known to be free of viral infection, and determining the first animal to be viral-infection positive if the level of expression of Mx protein in the first animal is significantly elevated compared to the level of expression of Mx protein in the second animal.

2. The method of claim 1 wherein the first animal is a mammal.

3. The method of claim 2 wherein the mammal is a member of the order perissodactyla or artiodactyla.

4. The method of claim 3 wherein the mammal is selected from the group consisting of cattle, sheep, goats, horses, swine, and llamas.

5. The method of claim 2 wherein the mammal is a member of the order carnivora.

6. The method of claim 5 wherein the mammal is a member of the family of canidae or felidae.

7. The method of claim 2 wherein the mammal is a primate.

8. The method of claim 7 wherein the primate is a human.

9. The method of claim 1 wherein the level of expression of Mx protein is determined by determining the level of mRNA coding for Mx protein.

10. The method of claim 9 wherein the determination of mRNA is by Northern blot analysis, slot-blot analysis, or polymerase chain reaction.

11. The method of claim 1 wherein the level of expression of Mx protein is determined by determining the level of Mx protein.

12. The method of claim 11 wherein the determination of the level of Mx protein is by evaluating the binding of an antibody to the protein or by an assay based on a function of the protein.

13. The method of claim 12 wherein the level of Mx protein is detected by a colorimetric assay.

14. The method of claim 1 wherein the level of expression of the protein is determined by determining the expression of the protein in a cell of the animal.

15. The method of claim 1 wherein the level of expression of the protein is determined by analyzing a bodily fluid of the animal.

* * * * *